United States Patent
Wang et al.

(10) Patent No.: US 6,180,629 B1
(45) Date of Patent: Jan. 30, 2001

(54) [4,5]-FUSED-1,3-DISUBSTITUTED-1,2-DIAZINE-6-ONE DERIVATIVES WITH NITROGEN CONTAINING SUBSTITUTENTS IN POSITION ONE FOR THE TREATMENT OF NEOPLASIA

(75) Inventors: Xiaojing Wang, Livermore, CA (US); Gerhard Sperl, Horsham, PA (US); Paul Gross, Stockton, CA (US); Rifat Pamukcu, Spring House; Gary A. Piazza, Doylestown, both of PA (US)

(73) Assignee: Cell Pathways, Inc., Horsham, PA (US)

( * ) Notice: Under 35 U.S.C. 154(b), the term of this patent shall be extended for 0 days.

(21) Appl. No.: 09/134,425

(22) Filed: Aug. 14, 1998

(51) Int. Cl.$^7$ .................. A61K 31/498; A61K 31/4985; C07D 237/34; C07D 403/12; C07D 471/04

(52) U.S. Cl. .................. 514/248; 514/234.2; 514/234.5; 514/241; 514/245; 544/117; 544/119; 544/212; 544/236; 544/237

(58) Field of Search .................... 544/116, 117, 544/236, 237, 119, 212; 514/234.2, 234.5, 248, 241, 245

(56) References Cited

U.S. PATENT DOCUMENTS

| | | | |
|---|---|---|---|
| 3,867,433 | 2/1975 | Shen et al. | 260/515 |
| 3,920,636 | 11/1975 | Takahasi et al. | 260/240 |
| 4,001,237 | 1/1977 | Partyka et al. | 260/256.4 |
| 4,001,238 | 1/1977 | Partyka et al. | 260/256.4 |
| 4,039,544 | 8/1977 | Broughton et al. | 260/256.4 |
| 4,060,615 | 11/1977 | Matier et al. | 424/251 |
| 4,079,057 | 3/1978 | Juby et al. | 260/256.5 |
| 4,098,788 | 7/1978 | Crenshaw et al. | 544/293 |
| 4,101,548 | 7/1978 | Crenshaw et al. | 544/284 |
| 4,102,885 | 7/1978 | Crenshaw et al. | 544/283 |
| 4,138,561 | 2/1979 | Crenshaw et al. | 544/284 |
| 4,146,718 | 3/1979 | Jenks et al. | 544/292 |
| 4,161,595 | 7/1979 | Kaplan et al. | 544/284 |
| 4,171,363 | 10/1979 | Crenshaw et al. | 424/251 |
| 4,208,521 | 6/1980 | Crenshaw et al. | 544/250 |
| 4,460,591 | 7/1984 | DeGraw et al. | 424/251 |
| 4,880,810 | 11/1989 | Lowe, III et al. | 514/258 |
| 4,885,301 | 12/1989 | Coates | 514/263 |
| 4,923,874 | 5/1990 | McMahon et al. | 514/258 |
| 5,073,559 | 12/1991 | Coates | 514/262 |
| 5,147,875 | 9/1992 | Coates et al. | 514/259 |
| 5,177,075 | 1/1993 | Suto et al. | 514/248 |
| 5,250,535 | 10/1993 | Verheyden et al. | 514/262 |
| 5,324,727 | 6/1994 | Iwase et al. | 514/234.5 |
| 5,401,774 | 3/1995 | Pamukcu et al. | 514/569 |
| 5,439,895 | 8/1995 | Lee et al. | 514/63 |
| 5,462,941 | 10/1995 | Iwase et al. | 514/248 |
| 5,614,627 | 3/1997 | Takase et al. | 514/293 |

FOREIGN PATENT DOCUMENTS

| | | |
|---|---|---|
| 274218 | 12/1989 | (DE) . |
| 43 43 286 A1 | 12/1993 | (DE) . |
| 0 347146 A2 | 12/1989 | (EP) . |
| 0 349239 A2 | 1/1990 | (EP) . |
| 0 351058 A1 | 1/1990 | (EP) . |
| 0 352960 A2 | 1/1990 | (EP) . |
| 0 395328 A2 | 10/1990 | (EP) . |
| 0 463756 A1 | 1/1992 | (EP) . |
| 0 526004 A1 | 2/1993 | (EP) . |
| 807826 | 1/1959 | (GB) . |
| 2063249 | 6/1981 | (GB) . |
| 1303 061 | 1/1993 | (GB) . |
| 57-167974 | 10/1982 | (JP) . |
| 5-32591 | 2/1993 | (JP) . |
| WO 92/03419 | 3/1992 | (WO) . |
| WO 93/07149 | 4/1993 | (WO) . |
| WO 93/12095 | 6/1993 | (WO) . |
| WO 94/05661 | 3/1994 | (WO) . |
| WO 94/15932 | 7/1994 | (WO) . |
| WO 95/08539 | 3/1995 | (WO) . |

OTHER PUBLICATIONS

Yassin, "Synthesis and Reactions of 2–amino–4–(substituted phenyl)–5,6,7, 8–tetrabromo–1–(2H)–phthalazinone derivatives," Pak. J. Sci. Ind. Res., vol. 37, No. 12, pp. 508–511, Dec. 1994.*

Tamura et al., "Chemical Properties of N–Benzoylimines of Quinazoline, Quinoxaline, and Phthalazine," J. Heterocyclic Chem., vol. 13, No. 1, pp. 23–28, Feb. 1976.*

Chaturvedi et al., "Synthesis of 1–(Substituted Thioanilido)–8–Keto—3–Substituted Benzopyridazines As Possible Cardiovascular Agents," Indian J. Pharm. Sci., vol. 50, No. 6, pp. 316–318, 1988.*

Kameoka et al., "A Specific T–Cell Subset with CD+/CD38–markers derived from HIV–1 carriers induces apoptosis in healthy donor–derived T–lymphocytes," Virus Research, vol. 56, No. 1, MEDLINE abstract provided, pp. 115–122, Jul. 1998.*

Tobin et al., "Do hair bulb melanocytes undergo apoptosis during hair follicle regression?", J. Invest. Dermatol., vol. 111, No. 6, MEDLINE abstract provided, pp. 941–947, Dec. 1998.*

Bayoumy et al., "Synthesis of some Oxadiazolo–, Oxadiazolino–, Thiadiazolo–and Triazolothiazinophthalzinone Derivatives," J. Chem. Soc. Pak., vol. 11, No. 4, pp. 302–308, 1989.*

Waddell, W.R. et al., Am. J. Surgery, vol. 157, pp. 175–179 (1989).

Moorghen, M. et al., Journal of Pathology, vol. 156, pp. 341–347 (1988).

Moorghen, M. et al., Acta Histochemica, Suppl.–Band XXIX, S. 195–199 (1990).

* cited by examiner

*Primary Examiner*—Richard L. Raymond
(74) *Attorney, Agent, or Firm*—Robert W. Stevenson

(57) ABSTRACT

[4,5]-Fused-1,3-disubstituted-1,2-diazine-6-one derivatives with nitrogen-containing substituents in position one are useful for inducing or promoting apoptosis and for arresting uncontrolled neoplastic cell proliferation, and are specifically useful in the arresting and treatment of neoplasia, including precancerous and cancerous lesions.

24 Claims, No Drawings

[4,5]-FUSED-1,3-DISUBSTITUTED-1,2-DIAZINE-6-ONE DERIVATIVES WITH NITROGEN CONTAINING SUBSTITUTENTS IN POSITION ONE FOR THE TREATMENT OF NEOPLASIA

TECHNICAL FIELD

This invention relates to compounds and methods for inducing or promoting apoptosis and for arresting uncontrolled neoplastic cell proliferation, methods that are specifically useful in the arresting and treatment of neoplasias, including precancerous and cancerous lesions.

BACKGROUND OF THE INVENTION

Pharmaceuticals that are effective against early stage neoplasias comprise an emerging and expanding area of research and potential commercial development. Such pharmaceuticals can delay or arrest development of precancerous lesions into cancers. Each year in the United States alone, untold numbers of people develop precancerous lesions, which exhibit a strong statistically significant tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), cervical dysplasia (cervical cancer) and other such neoplasms.

Such compounds and methods are particularly beneficial to sub-populations of patients who repeatedly develop precancerous lesions, and therefore have a statistically higher probability of getting cancer. Many cancer types (e.g., breast, colon, prostate etc.) have such patient sub-populations.

The search for drugs useful for treating and preventing neoplasias in their earliest stages is intensive because chemotherapy and surgery on cancer itself is often not effective, and current cancer chemotherapy has severe side effects. Such cancer-preventative compounds are also envisaged for recovered cancer patients who retain a risk of cancer reoccurrence, and even for cancer patients who would benefit from compounds that selectively induce apoptosis in neoplastic, but substantially not in normal cells.

Because it is believed that chronic administration of cancer-preventative pharmaceuticals is necessary to inhibit or arrest the development of neoplasia, standard cancer chemotherapeutic drugs are not considered appropriate drugs for cancer chemoprevention because whatever cancer preventative (as opposed to cancer-fighting) capabilities those drugs may possess do not outweigh their severe side effects. Most standard chemotherapeutics are now believed to kill cancer cells by inducing apoptosis (also sometimes referred to as "programmed cell death"). Apoptosis naturally occurs in many tissues in the body. Apoptosis plays a critical role in tissue homeostasis, that is, it ensures that the number of new cells produced are correspondingly offset by an equal number of cells that die. Apoptosis is especially pronounced in self-renewing tissues such as bone marrow, immune cells, gut, and skin. For example, the cells in the intestinal lining divide so rapidly that the body must eliminate cells after only three days to protect and prevent the overgrowth of the intestinal lining.

Standard chemotherapeutics promote apoptosis not only in cancer cells, but also in normal human tissues, and therefore have a particularly severe effect on tissues where apoptosis is especially pronounced (e.g. hair, gut and skin). The results of those effects include hair loss, weight loss, vomiting and bone marrow immune suppression. Thus, standard chemotherapeutics are inappropriate for cancer prevention, particularly if chronic administration is indicated.

Several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the continued prophylactic use of currently available NSAIDs, even in high colon cancer-risk patients, is still marked by severe side reactions that include gastrointestinal irritations, perforations, ulcerations and kidney toxicity believed to be produced by inhibition of prostaglandin synthetase activity ("PGE-2"). Such inhibition is a requirement for the NSAIDs anti-inflammatory action since elevated levels of PGE-2 are associated with inflammation. PGE-2 plays a protective function in the gastrointestinal tract, which is the reason such gastric side effects arise with chronic NSAID therapy, which is rarely indicated for arthritis sufferers, acute therapy being the norm for them. However, chronic administration of sulindac is important for high cancer-risk patients to eliminate and prevent future polyps which causes gastric side effects in many such patients. Once NSAID treatment is terminated due to such complications, the neoplasms return, particularly in high risk patients.

Compounds such as those disclosed in U.S. Pat. No. 5,643,959 have exhibited advantages in the treatment of neoplastic lesions since such compounds have been shown to induce apoptosis in neoplastic cells but not in normal cells in humans. Thus, the severe side effects due to induction of apoptosis in normal cells by conventional chemotherapeutics are avoided by these novel therapeutics (see, Van Stock, et al., *Gastroenterology*, 112 (4): A673, 1997). In addition, such compounds do not exhibit the gastric side effects associated with NSAIDs since such compounds do not substantially inhibit PGE-2. More potent compounds with such neoplasia specificity but without substantial PGE-2 activity are desirable.

SUMMARY OF THE INVENTION

This invention represents potent compounds that induce apoptosis in neoplastic cells (but not substantially in normal cells), for treating patients with neoplastic lesions without substantially inhibiting PGE-2. This invention also involves methods for inducing such specific apoptosis in neoplastic cells by exposing such cells to a pharmacologically effective amount of those compounds described below to a patient in need of such treatment. Such compositions are effective in modulating apoptosis and modulating the growth of neoplasms.

DETAILED DESCRIPTION OF THE INVENTION

As discussed above, the present invention includes compounds of Formula I below (as well as their pharmaceutically acceptable salts) for treating a patient with neoplastic, particularly precancerous, and cancerous lesions:

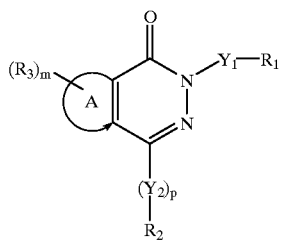

wherein Y₁ is selected from the group consisting of —(CH₂)ₙ—C(X)—NH—, —NH—, —NH—C(X)—, —NH—C(X)—O—, and —NH—C(X)—NH—; where X is oxygen or sulfur: and n is an integer from 0 to 3;

R₁ and R₂ are independently selected from the group consisting of substituted or unsubstituted phenyl, benzyl, pyridinyl, pyrrolyl, pyrrolidinyl, pyrazolyl, pyrazolidinyl, imidazolyl, imidazolidinyl, piperidinyl, pyrazinyl, piperazinyl, pyrimidinyl, morpholinyl, tetrazolyl, triazinyl, furfuryl and thiophenyl, wherein the said substituents are one to three independently selected from the group consisting of halogen, lower alkyl, lower alkoxy, amino, lower alkylamino, di-lower alkylamino, hydroxy, nitro, nitrile, —CO₂H, —SO₂NH₂ lower alkyl mercapto, and lower alkyl sulfonyl;

Y₂ is selected from the group consisting of lower alkylene, lower (hydroxy) alkylene, lower (amino) alkylene, lower (alkylamino) alkylene, carbonyl, and —CH₂—NH—;

A is a ring fused with the pyridazine ring selected from the group consisting of benzene, pyridine, pyrrole, pyrrolidine, pyrazole, pyrazolidine, imidazole, imidazolidine, piperidine, pyrazine, piperazine, pyrimidine, morpholine, tetrazole, triazine, furane and thiophene;

R₃ is independently selected in each instance from the group consisting of halogen, lower alkyl, lower alkoxy, amino, lower alkylamino, di-lower alkylamino, hydroxy, nitro, nitrile, carboxyl, sulfonylamide, lower alkyl mercapto, and lower alkyl sulfonyl.

m is an integer from 0 to four;

p is 0 or 1;

and pharmaceutically acceptable salts thereof.

Preferred compounds useful in methods of this invention include those wherein (1) A is selected from the group consisting of condensed benzene, pyridine, pyrrole, pyrrolidine, imidazolidine, piperidine, pyrazine, piperazine, pyrimidine, morpholine, triazine, furane and thiophene; (2). R₁ is selected from the group consisting of substituted or unsubstituted phenyl, benzyl, pyridinyl, pyrrolyl, pyrazinyl, pyrimidinyl, morpholinyl, tetrazolyl, triazinyl, furfuryl and thiophenyl, wherein said substituents are one or two independently selected from the group consisting of halogen, lower alkyl, lower alkoxy, di-lower alkylamino, hydroxy, nitrile, —CO₂H, —SO₂NH₂, lower alkyl mercapto, and lower alkyl sulfonyl; (3) R₂ is selected from the group consisting of substituted or unsubstituted phenyl, benzyl, pyridinyl, pyrrolyl, pyrazolyl, imidazolyl, pyrazinyl, pyrimidinyl, morpholinyl, triazinyl, furfuryl and thiophenyl, wherein said substituents are one, two, or three independently selected from the group consisting of halogen, lower alkyl, lower alkoxy, di-lower alkylamino, hydroxy, nitro, lower alkyl mercapto, and lower alkyl sulfonyl; (4) Y₁ is selected from the group consisting of —(CH₂)ₙ—C(X)—NH—, —NH—C(X)—NH—,—NH—, —NH—C(X)—, and —NH—C(X)—O—; where X is oxygen or sulfur and n is 0, 1 or 2; (5) Y₂ is selected from the group consisting of lower alkylene, lower (hydroxy) alkylene, carbonyl, and —CH₂—NH—; (6) p is 0 or 1; and (7) wherein R₃ is independently selected in each instance from the group consisting of halogen, lower alkyl, lower alkoxy, di-lower alkylamino, hydroxy, —CO₂H, —SO₂NH₂, lower alkyl mercapto, and lower alkyl sulfonyl; and m is an integer from 0 to 2.

The most preferred compounds useful in methods of this invention include those wherein (1) A is selected from the group consisting of benzene, pyridine, pyrazine, pyrimidine, furane and thiophene (2) R₁ is selected from the group consisting of substituted or unsubstituted phenyl, benzyl, pyridinyl, pyrazinyl, pyrimidinyl, furfuryl and thiophenyl, wherein said substituent is one selected from the group consisting of halogen, lower alkyl, lower alkoxy, di-lower alkylamino, nitrile, —SO₂NH₂,and lower alkyl mercapto; (3) R₂ is selected from the group consisting of substituted or unsubstituted phenyl, benzyl, pyridinyl, pyrazinyl, pyrimidinyl, triazinyl, furfuryl and thiophenyl, wherein said substituent is one or three selected from the group consisting of halogen, lower alkyl, lower alkoxy, di-lower alkylamino, and lower alkyl mercapto; (4) Y₁ is selected from the group consisting of —(CH₂)ₙ—C(X)—NH— and —NH—C(X)—NH—; where X is oxygen and n is 0 or 1; (5) Y₂ is selected from the group consisting of lower alkylene, carbonyl, and —CH₂—NH—; (6) p is 0; and (7) wherein R₃ is selected from the group consisting of halogen, lower alkyl, lower alkoxy, di-lower alkylamino, and lower alkyl mercapto; and m is 0 or 1.

The present invention is also a method of treating individuals with neoplastic lesions by administering a pharmacologically effective amount of an enterically coated pharmaceutical composition that includes compounds of this invention.

Preferably, such compounds are administered without therapeutic amounts of an NSAID.

Also, the present invention is a method of inhibiting the growth of neoplastic cells by exposing the cells to an effective amount of compounds of Formula I.

In still another form, the invention is a method of inducing apoptosis in human cells by exposing those cells to an effective amount of compounds of Formula I where such cells are sensitive to these compounds.

Additionally, in yet another form, the invention is a method of treating a patient having a disease which would benefit from regulation of apoptosis by treating the patient with an effective amount of compounds of Formula I. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

As used herein, the term "precancerous lesion" includes syndromes represented by abnormal neoplastic, including dysplastic, changes of tissue. Examples include dysplasic growths in colonic, breast, bladder or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, prostatic dysplasia, bronchial dysplasia, breast, bladder and/or skin and related conditions (e.g., actinic keratosis), whether the lesions are clinically identifiable or not.

As used herein, the term "cancerous" refers to lesions that are malignant. Examples include malignant melanomas, breast cancer, prostate cancer and colon cancer.

As used herein, the term "neoplasm" refers to both precancerous and cancerous lesions and hyperplasia.

As used herein, the term "halo" or "halogen" refers to chloro, bromo, fluoro and iodo groups, and the term "alkyl" refers to straight, branched or cyclic alkyl groups and to substituted aryl alkyl groups. The term "lower alkyl" refers to $C_1$ to $C_8$ alkyl groups.

The term "lower alkoxy" refers to alkoxy groups having from 1 to 8 carbons, including straight, branched or cyclic arrangements.

The term "lower alkylmercapto" refers to a sulfide group that is substituted with a lower alkyl group; and the term "lower alkyl sulfonyl" refers to a sulfone group that is substituted with a lower alkyl group.

The term "pharmaceutically acceptable salt" refers to non-toxic acid addition salts and alkaline earth metal salts of the compounds of Formula I. The salts can be prepared in situ during the final isolation and purification of such compounds, or separately by reacting the free base or acid functions with a suitable organic acid or base, for example. Representative acid addition salts include the hydrochloride, hydrobromide, sulfate, bisulfate, acetate, valerate, oleate, palmetate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali and alkaline earth metal salts include the sodium, calcium, potassium and magnesium salts.

It will be appreciated that certain compounds of Formula I can possess an asymmetric carbon atom and are thus capable of existing as enantiomers. Unless otherwise specified, this invention includes such enantiomers, including any racemates. The separate enantiomers may be synthesized from chiral starting materials, or the racemates can be resolved by conventional procedures that are well known in the art of chemistry such as chiral chromatography, fractional cyrstallization of diastereomeric salts and the like.

Compounds of Formula I also can exist as geometrical isomers (Z and E); the Z isomer is preferred.

Compounds of this invention may be formulated into pharmaceutical compositions together with pharmaceutically acceptable carriers for oral administration in solid or liquid form, or for rectal or topical administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for rectal administration are preferably suppositories that may contain, in addition to the compounds of this invention excipients such as cocoa butter or a suppository wax, or gel.

The pharmaceutically acceptable carrier and compounds of this invention are formulated into unit dosage forms for administration to a patient. The dosage levels of active ingredient (i.e., compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The pharmaceutical compositions of this invention are preferably packaged in a container (e.g., a box or bottle, or both) with suitable printed material (e.g., a package insert) containing indications, directions for use, etc.

The scheme for producing compounds useful in this invention is illustrated and explained below.

Scheme I

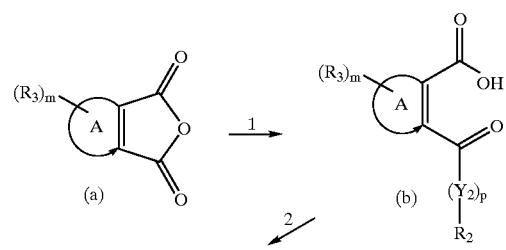

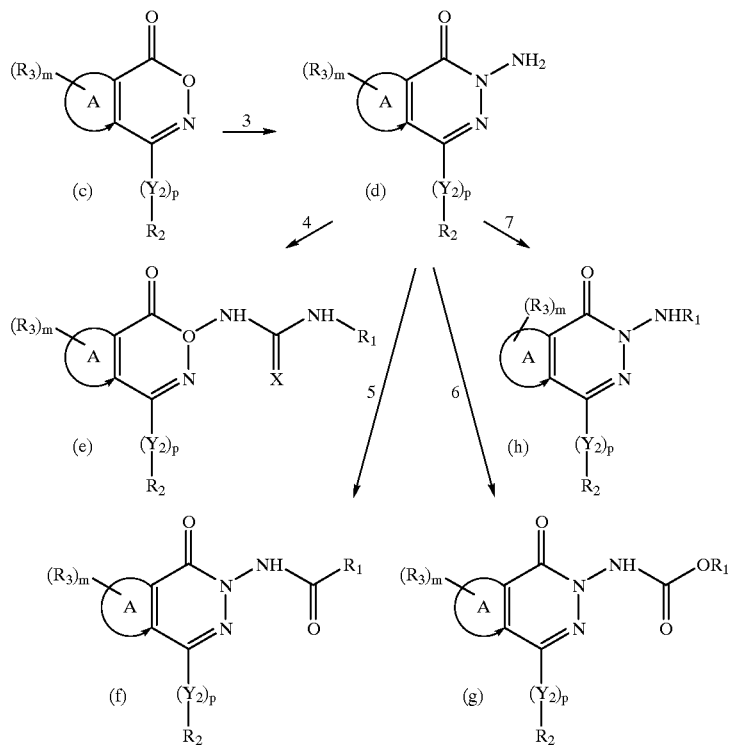

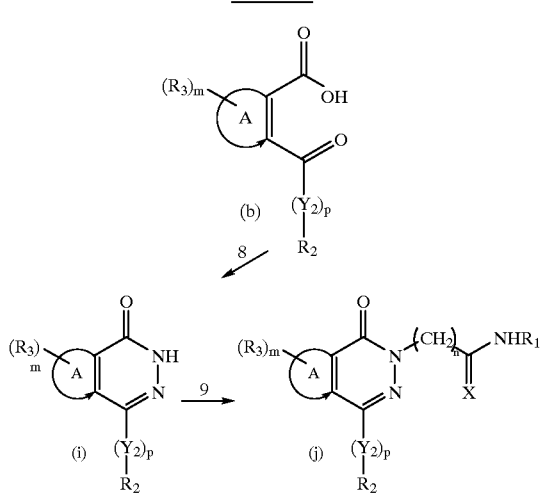

A γ-ketocarboxylic acid (b) can be obtained from a substituted or unsubstituted anhydride (a) by Friedel-Crafts reaction with a substituted or unsubstituted aromatic compound ($R_2$—$H_1$ Method A) (OS CVI, 517, 1941) or by with a Grignard reagent (Hal-Mg—$(Y_2)_p$—$R_2$) followed by acidic workup (Method B).

The γ ketocarboxylic acid (b) is refluxed in pyridine with hydroxylamine for several hours to obtain the oxazinone derivative (c) (see reaction 2; Indian J. Chem. Sec. B, 1994, Vol. 33B, 742–746) which is then condensed with hydrazine to yield the corresponding pyridazine derivative (d) (reaction 3).

The pyridazine (d) is derivatised to different products (e–h). Ureas or thioureas are generated from substituted isocyanates ($R_1N$=C=O) or from substituted isothiocyanates ($R_1N$=C=S), respectively (see reaction 4). The reaction of the pyridazine (d) with a substituted acid chloride leads to an amide (f) (reaction 5).

The reaction with a substituted halo ester generates the urethane (g) (reaction 6), and the reaction with alkylhalides leads to substituted amines (h) (reaction 7).

To obtain N-substituted acetamides and its homologues (j), Scheme II is employed. Condensation of acid (b) with hydrazine leads to the corresponding pyridazine derivative (i), (reaction 8). After treatment with base (e.g., KOH) a $S_N$-reaction with a substituted amido or thioamido halide generates the product (j).

In summary, the reagents and conditions for Scheme I and II are as follows:

(1) Method A: Friedel-Crafts-Reaction, $R_2H$ and $AlCl_3$ as a catalyst. Method B: Grignard Reaction Hal-Mg$(Y)_p$—$R_2$, acid
(2) $NH_2OH$, reflux
(3) $NH_2NH_2$
(4) $R_1N$=C=X, where X is O or S
(5) $R_1$—C(O)—Cl
(6) $R_1O$—C(O)-Hal
(7) $R_1H$-Hal
(8) $NH_2NH_2$
(9) Hal-$(CH_2)_n$—C(X)—$NHR_1$, where X is O or S A number of γ-ketocarboxylic acids (b) are commercially available (e.g., from Aldrich Chemical Co.)

2-benzoylbenzoic acid
2[4-(dibutylamino)-2-hydroxybenzoyl]benzoic acid
3-benzoyl-2-pyridine carboxylic acid
2-acetylbenzoic acid
2-(4-fluuorobenzoyl)benzoic acid
2-aminobenzophenone-2'-carboxylic acid
2 (3-amino-4-chlorobenzoyl)benzoic acid 4-[4-(2-carboxybenzoyl)phenyl]butyric acid
2-(4-chlorobenzoyl)benzoic acid The foregoing may be better understood from the following examples that are presented for the purposes of illustration and are not intended to limit the scope of the invention. As used in the following examples, the references to substituents such as R1 Y, A, etc. refer to the corresponding substituents in Formula I above.

EXAMPLE 1

2-(1-Oxo-4-Phenylphthalazin-2-yl)-N-Benzylethanamide (A) 1-Hydroxy-4-phenylphthalazine A 3 M solution of hydrazine (0.15 mol) in ethanol is added to a solution of α-benzoyl benzoic acid (11.3 g; 0.05 mol) in ethanol (100 ml). The mixture is stirred at room temperature for 5 hours. Precipitation yields 1-hydroxy-4-phenylphthalazine as a white solid (12.3 g)(m.p. 240° C.).

(B) 2-(1-Oxo-4-phenylphthalazin-2-yl)-N-benzylethanamide

1N NaOH (4.5 mmol) is added to 1-hydroxy-4-phenylphthalazine (1 g, 4.5 mmol) in ethanol (20 ml). After 15 minutes, N-benzyl bromoacetamide (1.32 g, 4.5 mmol) is added, the reaction mixture is diluted with ethanol (20 ml) and is stirred overnight. Filtration followed by washing with ethanol (50 ml) and then with water (50 ml) yields the title compound (0.67 g). ($R_1$=benzyl, $R_2$=phenyl, A=benzene, $Y_1$=—$CH_2$—C(O)—NH—, m=0, p=0).

EXAMPLE 2

2-[4-(4-Fluorophenyl)-1-Oxo-Phthalazin-2-yl)]-N-Benzylethanamide (A) 4-Fluorophenylphthalazine-1-one 2-(4-fluorobenzoyl)benzoic acid (5 g; 20.47 mmol) is suspended in ethanol (100 ml). Hydrazine (3 M in ethanol; 60 mmol) is added, and the mixture is stirred at room temperature for 4 days. A white solid precipitates, is filtered off and is washed with ethanol (20 ml). Yield: 3.20 g of 4-fluorophenylphthalazine-1-one.

(B) 2-[4-(4-Fluorophenyl)-1-oxo-phthalazin-2-yl]-N-benzylethanamide

Following the procedure described in Example 1, part B, the 4-fluorobenzyl-phthalazine-1-one is used instead of 1-hydroxy-4-phenyl phthalazine to yield the title compound. ($Y_1$=$CH_2$—C(O)—NH, $R_1$=benzyl, p=0, $R_2$=p-fluorophenyl, m=0, A=benzene).

EXAMPLE 3

2-[4-(4-Chlorophenyl)-1-Oxo-Phthalazin-2-yl]-N-Benzylethanamide

A. 4-(Chlorophenyl)phthalazine-1-one

Following the procedure described in Example 2 part A, 2 (4-chlorobenzoyl)benzoic acid (5 g, 19.18 mmol) is used instead of 2(4-fluorobenzoyl)benzoic acid to yield 4-(chlorophenyl)phthalazine-1-one (3.75 g).

B. 2-[4-(4-Chlorophenyl)-1-oxo-phthalazin-2-yl]-N-benzylethanamide

Following the procedure described in Example 2 part B, 4-chlorophenyl-phthalazine-1-one (1.16 g, 4.5 mmol) is used instead of 4-fluorophenyl-phthalazine-1-one to yield [4-(4-chlorophenyl)-1-oxo-phthalazin-2-yl]-N-benzylethanamide ($Y_1$=$CH_2$—C(O)—NH, $R_1$,=benzyl, p=0, $R_2$=p-chlorophenyl, m=0, A=phenyl).

EXAMPLE 4

2-[1-Oxo-4-(Pyridin-2-yl)-Phthalazin(-2-yl)]-N-Benzylethanamide

A. 2-(2-Pyridin-2-yl-carbonyl)benzoic acid

A Grignard solution of 2-bromomagnesium pyridine (4.55 g, 25 mmol) in ether is added to phthalic anhydride (7.4 g, 50 mmol) in ether. The reaction mixture is stirred under reflux for 2 hours, cooled with ice and is then hydrolysed with HCl to yield 2-(2-pyridin-2-yl-carbonyl)benzoic acid.

B. 1-Hydroxy-4-(Pyridin-2-yl)phthalazine

A 3M-solution of hydrazine (20 ml, 60 mmol) in ethanol is added to a solution of 2-(2-pyridin-2-yl-carbonyl)benzoic acid (4,54 g, 20 mmol), and the mixture is stirred at room temperature for 5 hours. Precipitation yields 1-hydroxy-4-(pyridin-2-yl)phthalazine.

C. 2-[1-oxo-4-(pyridin-2-yl)phthalazin-2-yl)]-N-benzylethanamide

The product from the part B of this example is subjected to the general procedure of Example 1, part B to yield 2-[1-oxo-4-(pyridin-2-yl)phthalazin-2-yl)]-N-benzylethanamide. ($R_1$=3-benzyl, $R_2$=pyridin-2-yl, A=benzene, $Y_1$=$CH_2$—C(O)—NH, m=0, p=0).

EXAMPLE 5

2-[1-Oxo-4-(Pyrimidin-5-yl)-(2H)-Phthalazin-2-yl)]-N-Benzylethanamide

The general procedure described in Example 4, part A is followed with phthalic anhydride and 5-bromomagnesium pyrimidine in ether to yield 2-(pyrimidin-5-yl-carbonyl) benzoic acid. The general procedures of parts B and C in Example 4are followed to produce the title compound, 2-[1-oxo-4-(pyrimidin-5-yl)-(2H)-phthalazin-2-yl)]-N-benzylethanamide ($R_1$=benzyl, $R_2$=pyrimidin-5-yl, A=benzene, m=0, p=0, $Y_1$=$CH_2$—C(O)—NH).

EXAMPLE 6

2-[1-Oxo-4-(Pyridin-3-yl)-(2H)-Phthalazin-2-yl)]-N-Benzylethanamide

The general procedure described in Example 4, part A is followed with phthalic anhydride and 5-bromo magnesium pyridine in ether to yield 2-(pyrimidin-5-yl-carbonyl) benzoic acid. The general procedures of parts B and C in Example 4 are followed to produce the title compound, 2-[1-oxo-4-(pyridin-3-yl)-(2H)-phthalazin-2-yl)]-N-benzylethanamide ($R_1$=benzyl, $R_2$=pyridin-3-yl, A=benzene, m=0, p=0, $Y_1$=$CH_2$—C(O)—NH).

EXAMPLE 7

2-[1-Oxo-4-(Thiophen-2-yl)-(2H)-Phthalazin-2-yl)]-N-Benzylethanamide

The procedure described in Example 4, part A is followed with phthalic anhydride and 3-bromomagnesium pyridine in ether to yield 2-(pyridin-3-yl-carbonyl)benzoic acid. The general procedure of parts B and C in Example 4 are followed to achieve the title compound, 2-[1-oxo-4-(thiophen-2-yl)-(2H)-phthalazin-2-yl)]-N-benzylethanamide ($R_1$=benzyl, $R_2$=thiophen-2-yl, A=benzene, m=0, p=0, $Y_1$=CH$_2$—C(O)—NH).

EXAMPLE 8

2-[1-Oxo-4-Phenyl-2-Hydro-5-Azaphthalazin-2-yl)]-N-Benzylethanamide

A. 4-Phenyl-1,2-dihydro-5-azaphthalazin-1-ol

A 3M ethanolic solution of hydrazine (20 ml, 60 mmol) is added to an ethanolic solution of 2-benzoyl-3-pyridine carboxylic acid (4.54 g, 20 mmol), and the mixture is stirred at room temperature for 5–24 hours. Precipitation yields 4-phenyl-1,2-dihydro-5-azaphthalazin-1-ol.

B. 2-[1-Oxo-4-phenyl-2-hydro-5-azaphthalazin-2-yl)]-N-benzylethanamide

The general procedure, described in Example 1, part B is followed with 4-phenyl-1,2-dihydro-5-azaphthalazin-1-ol as the starting material to obtain the title compound. ($R_1$=benzyl, $R_2$=phenyl, A=pyridine, m=0, p=0, $Y_1$=CH$_2$—C(O)—NH).

EXAMPLE 9

2-[1-Oxo-4-(4-Fluorobenzyl)-(2H)-Phthalazin-2-yl)]-N-Benzylethanamide

A. 2-(4-Fluorobenzyl carbonyl)benzoic acid

4-Fluorobenzyl magnesium chloride (4.6 g, 25 mmol) in ether is added to phthalic acid (7.4 g, 50 mmol) in ether. The reaction mixture is stirred under reflux for 2 hours, is cooled with ice and is hydrolysed with HCl to yield 2-(4-fluorobenzylcarbonyl)benzoic acid.

B. 4-(4-Fluorobenzyl)-1-hydroxy-phthalazine

A 3 M ethanolic solution of hydrazine (20 ml, 60 mmol) is added to 2-(4-fluorobenzyl carbonyl)benzoic acid (5.5 g, 20 mmol), and the mixture is stirred at room temperature for 5 hours. Precipitation gives 4-(4-fluorobenzyl)-1-hydroxy-phthalazine.

C. 2-[1-Oxo-4-(4-fluorobenzyl)-(2H)-phthalazin-2-yl)]-N-benzylethanamide

The product of the previous reaction (B) is subjected to the general procedure of Example 1, part B to yield 2-[1-oxo-4-(4-fluorobenzyl)-(2H)-phthalazin-2-yl)]-N-benzylethanamide. ($R_1$=benzyl, $R_2$=4-chlorophenyl, A=benzene, m=0, p=1, $Y_1$=CH$_2$—C(O)—NH, $Y_2$=CH$_2$).

EXAMPLE 10

2-[1-Oxo-4-(4-Pyridylmethyl)-1-(2H)-Phthalazin-2-yl)]-N-Benzylethanamide

A. 3-(4-Pyridylmethylene)-isobenzofuran-1-one

In accordance with the procedure described in Lombardino, J.O.C. Vol. 32, pp. 1988–1992 (1967), a solution of isobenzofuran-1-one (13.4 g, 0.1 mol) and 4-pyridine carboxaldehyde (10.7 g, 0.1 mol) in 100 ml dry methanol are refluxed for 2 hours. The solvent is evaporated, and the product (3-(4-pyridylmethylene)isobenzofuran-1-one is used in the next step without further purification.

B. 4-(4-Pyridylmethyl)-1-(2H)-phthalazinone

The general procedure described in Example 9, part B is followed with 3-(4-pyridylmethylene)-isobenzofuran-1-one instead of 2-(4-fluorobenzylcarbonyl)benzoic acid as the starting material to yield 4-(4-pyridylmethyl)-1-(2H)-phthalazinol.

C. 2-[1-Oxo-4-(4-pyridylmethyl)-1-(2H)-phthalazin-2-yl)]-N-benzylethanamide

The product of the previous reaction (B) is subjected to the general procedure of Example 1, part B to yield 2-[1-oxo-4-(4-pyridylmethyl)-1-(2H)-phthalazin-2-yl)]-N-benzylethanamide ($R_1$=benzyl, $R_2$=4-pyridinyl, A=benzene, m=0, p=1, $Y_1$=CH$_2$—C(O)—NH, $Y_2$=CH$_2$).

EXAMPLE 11

2-[1-Oxo-4-(3-Pyridylmethyl)-1-(2H)-Phthalazin-2-yl)]-N-Benzylethanamide

A. 3-(3-Pyridylmethylene)isobenzofuran-1-one

Following the procedure described in Example 10, part A, the 3-pyridinecarboxaldehyde is used instead of the 4-pyridinecarboxaldehyde to give the title product.

B. 4-(3-Pyridylmethyl)-1-(2H)-phthalazinol

The procedure described in Example 10, part B is followed with 3-(3-pyridylmethylene)isobenzofuran-1-one instead of 3-(4-pyridylmethylene)isobenzofuran-1-one as the starting material.

C. 2-[1-Oxo-4-(3-pyridylmethyl)-1-(2H)-phthalazin-2-yl)]-N-benzylethanamide

The product of the previous reaction (B) is subjected to the general procedure of Example 1, part B to yield the title compound ($R_1$=benzyl, $R_2$=3-pyridinyl, A=benzene, m=0, p=1, $Y_1$=CH$_2$—C(O)—NH, $Y_2$=CH$_2$).

EXAMPLE 12

2-[1-Oxo-4-(2-Pyridylmethyl)-(2H)-Phthalazin-2-yl)]-N-Benzylethanamide

A. 3-(2-Pyridylmethylene)isobenzofuran-1-one

With the general procedure described in Example 10, part A. 2-pyridine carboxaldehyde is used instead of 4-pyridine carboxaldehyde to give 3-(2-pyridylmethylene)-isobenzofuran-1-one.

B. 4-(3-Pyridylmethyl)-1-(2H)-phthalazinol

With the procedure described in Example 10, part B, 3-(2-pyridylmethylene)isobenzofuran-1-one is used as the starting material instead of 3-(4-pyridylmethylene)isobenzofuran-1-one to give the title compound.

C. 2-[1-Oxo-4-(2-pyridylmethyl)-(2H)-phthalazin-2-yl)]-N-benzylethanamide 4-(3-pyridylmethyl)-1-(2H)-phthalazinol is subjected to the general procedure of Example 1, part B to yield 2-[1-oxo-4-(2-pyridylmethyl)-(2H)-phthalazin-2-yl)]-N-benzylethanamide ($R_1$=benzyl, $R_2$=2-pyridinyl, A=benzene, m=0, p=1, $Y_1$=CH$_2$—C(O)—NH, $Y_2$=CH$_2$).

EXAMPLE 13

2-[1-Oxo-4-Benzyl-(2H)-Phthalazin-2-yl)]-N-Benzylethanamide

4-Benzyl-1-(2H)-phthalazinone is synthesized according to Chem. Pharm. Bull 39, pp. 2009–2015 (1991). It is then subjected to the general procedure Example 1, part B to yield the title compound. ($R_1$=benzyl, $R_2$=phenyl, A=benzene, m=0, p=1, $Y_1$=CH$_2$—C(O)—NH, $Y_2$=CH$_2$).

EXAMPLE 14

2-[(Benzylamino)Thioxomethylamino]-4-Phenyl-(2H)-1-Phthalazinone

A. 4-Phenylbenzo[d]1,2-oxazin-1-one (Ind. J. Chem., 1994, 33B, pp. 742–746)

A mixture of o-benzoyl benzoic acid (0.01 mol) and hydroxylamine hydrochloride (0.01 mol) is refluxed in pyridine (40 ml) for 3 hours, is cooled, and is poured over ice-cold dilute-HCl. The separated solid is filtered off, is dried and is crystallized from ethanol to give the title compound.

B. 2-Amino-4-phenyl-(2H)-1-phthalazinone (Ind. J. Chem., 1994, 33B, pp. 742–746)

A mixture of the benzoxazinone of part A above (0.01 mol) and hydrazine hydrate (0.01 mol) is refluxed in n-butanol for 6 hours. The mixture is filtered hot, is concentrated, and is cooled in an ice bath. The separated solid is filtered off, is dried and is recrystallized from toluene to give 2-amino-4-phenyl-(2H)-1-phthalazinone.

C. 2-[(Benzylamino)thioxomethylamino]4-phenyl-(2H)-1-phthalazinone

To a solution of 2-amino-4-phenyl-(2H)-1-phthalazinone (0.01 mol) in ethanol (40 ml) benzylisothiocyanate (0.01 mol) is added, and the mixture is refluxed for 6 hours. The precipitate is washed with cold ethanol and is recrystallized from ethanol to yield the title compound ($R_1$=benzyl, $Y_1$=NH—C(S)—NH, $R_2$=phenyl, A=benzene, p=0, m=0).

EXAMPLE 15

2-[(Phenylamino)Thioxomethylamino]4-Phenyl-(2H)-1-Phthalazinone

A mixture of the benzoxazinone of Example 14, part A (0.01 mol) and 4-phenyl-3-thiosemicarbazide (0.01 mol) is refluxed in n-butanol for 6 hours. The mixture is filtered hot, is concentrated, and is cooled in an ice-bath. The precipitate is filtered, is dried and is recrystallized to give the title compound ($R_1$=phenyl, $Y_1$=NH—C(S)—NH, $R_2$=phenyl, A=benzene, m=0, p=0).

EXAMPLE 16

N-[1-Oxo-4-Phenyl-(2H)-Phthalazin-2-yl]-N'-Benzylurea

The general procedures described in Example 14 are followed with benzylisocyanate instead of benzylisothiocyanate as the reagent in part C of Example 14, to obtain the title product, N-[1-oxo-4-phenyl-(2H)-phthalazin-2-yl]-N'-benzylurea ($R_1$=benzyl, $Y_1$=NH—C(O)—NH, $R_2$=phenyl, A=benzene, m=0, p=0).

EXAMPLE 17

N-[1-Oxo-4-Phenyl-(2H)-Phthalazin-2-yl]-O-Benzylcarbamate

The general procedures described in Example 14, parts A and B are followed. The obtained 2-amino-4-phenyl-(2H)-1-phthalazinone (0.01 mol) is stirred with aqueous NaHCO$_3$ and benzylchloroformate (0.01 mol) in dichloromethane at room temperature overnight. The organic phase is washed with water, dried over Na$_2$SO$_4$ and dichloromethane is evaporated. The obtained solid is recrystallized to give the title product, N-[1-oxo-4-benzyl-(2H)-phthalazin-2-yl]-O-benzylcarbamate ($R_1$=benzyl, $Y_1$=NH—C(O)—O, $R_2$=phenyl, A=benzene, m=0, p=0).

EXAMPLE 18

N-(1-Oxo-4-Phenyl-(2H)-Phthalazin-2-yl)-Benzamide

The general procedures described in Example 14, parts A and B are followed. The obtained 2-amino-4-phenyl-(2H)-1-phthalazinone (0.01 mol) is stirred with aqueous NaHCO$_3$ and benzoylchloride (0.01 mol) in dichloromethane at room temperature overnight. The organic phase is washed with water, dried over Na$_2$SO$_4$ and dichloromethane is evaporated. The product is recrystallized to yield the title compound, N-(1-oxo-4-phenyl-(2H)-phthalazin-2-yl) benzamide ($R_1$=benzyl, $Y_1$=NH—C(O), $R_2$=phenyl, A=phenyl, m=0, p=0).

EXAMPLE 19

N-[1-Oxo-(2H)-4-(2-Pyridinyl)-Phthalazin-2-yl] Thienylformamide

A. 4-(2-Pyridinyl)-benzo[d]1,2-oxazin-1-one

The procedure described in Example 14, part A is followed with 2-(2-pyridin-2-yl-carbonyl)benzoic acid (from Example 4, part A) as a starting material to obtain the title compound.

B. 2-Amino-4-(2-pyridinyl)-(2H)-1-phthalazinone

The procedure described in Example 14, part B is followed with 4-pyridin-2-yl-benzo[d]1,2-oxazin-1-one as the starting material to yield 2-amino-4-pyridin-2-yl-(2H)-1-phthalazinone.

C. N-[1-Oxo-(2H)-4-(2-pyridinyl)phthalazin-2-yl]2-thienylformamide

The product of part B, 2-amino-4-(2-pyridinyl)-(2H)-1-phthalazinone (0.01 mol), is stirred overnight with 2-thiophencarbonylchloride and with aqueous NaHCO$_3$ in dichloromethane at room temperature. The organic phase is washed with water, dried over Na$_2$SO$_4$ and dichloromethane is evaporated. The product is recrystallized to yield the title compound ($R_1$=2-thiophenyl, $Y_2$=NH—C(O), $R_2$=2-pyridinyl, A=benzene, m=0).

EXAMPLE 20

[(2-Thienylmethyl]Aminol-1-Oxo-(2H)-4-(Pyrimidin-5-yl)Phthalazine

A. 2-Amino-4-(pyrimidin-5-yl)-(2H)-1-phthalazinone

The general procedure described in Example 4, part A is followed with phthalic anhydride and 5-bromomagnesium pyrimidine in ether to yield 2-(pyrimidin-5-yl-carbonyl) benzoic acid. The general procedures of parts A and B in Example 19 are followed to produce 2-amino-4-(pyrimidin-5-yl)-(2H)-1-phthalazin-one.

B. 2-[(2-Thienylmethyl)amino]-1-oxo-(2H)-4-(pyrimidin-5-yl)phthalazine

The procedure described in Example 19, part C is followed with 2-thiophene methyl chloride (0.005 mol) (generated from 2-thiophene methanol by reaction with triphenylphosphine in carbon tetrachloride) as the alkylating reagent to give 2-[(2-thienylmethyl)amino]-1-oxo-(2H)-4-(pyrimidin-5-yl)phthalazine ($R_1$=2-thienylmethyl, $Y_1$=NH—, $R_2$=pyrimidin-5-yl, A=benzene, m=0, p=0).

EXAMPLE 21

N-[1-Oxo-(2H)-4-(Thiophen-2-yl)Phthalazin-2-yl]-2-Thiophenamide

The procedure described in Example 4, part A is followed with phthalic anhydride and 3-bromomagnesium thiophene in ether to yield 2-(thiophen-2-yl-carbonyl)benzoic acid. The general procedure of parts A and B in Example 19 are followed to achieve the title compound, N-[1-oxo-4-(thiophen-2-yl)-phthalazin-2-yl]-2-thiophenamide ($R_1$=2-thiophenyl, $Y_1$=NH—C(O), $R_2$=thiophen-2-yl, A=benzene, m 0, p=0).

EXAMPLE 22

2-[(Benzylamino)Thioxomethylamino]-4-(Pyrimidin-5-yl]-(2H)-1-Phthalazinone

The general procedure described in Example 4, part A is followed with phthalic anhydride and 5-bromo magnesium pyrimidine in either to yield 2-(pyrimidin-5-yl-carbonyl) benzoic acid. The general procedures of parts A, B and C in Example 14 are followed to produce the title compound, 2-[(benzylamino)thioxomethylamino]-4-(pyrimidine-5-yl]-(2H)-1-phthalazinone ($R_1$=benzyl, $Y_1$=NH—C(S)—NH, $R_2$=pyrimidin-5-yl, A=benzene, m=0, p=0).

EXAMPLE 23

2-[(Benzylamino)Thioxomethylamino]-4-Phenyl-2-Hydro-5-Azaphthalazin-1-One

A. 2-Amino-4-phenyl-(2H)-5-azaphthalazin-1-one

The procedure described in Example 14, part A is followed with 2-benzoyl-3-pyridine carboxylic acid as the starting material to give 2-amino-4-phenyl-(2H)-5-azaphthalazin-1-one.

B. 2-[(Benzylamino)thioxomethylamino]-4-phenyl-2-hydro-5-azaphthalazin-1-one

The general procedures described in Example 14, part C is followed 2-amino-4-phenyl-(2H)-5-azaphthalazin-1-one as the starting material to obtain the title compound ($R_1$=benzyl, $Y_2$=NH—C(S)—NH, $R_2$=phenyl, A=pyridine, m=0, p=0).

EXAMPLE 24

N-(4-(4-Fluorobenzyl)-1-Oxo-(2H)-Phthalazin-2-yl) Benzylcarbamate

The procedures described in Example 17, parts A, B and C are followed with 2-(4-fluorobenzyl carbonyl)benzoic acid from Example 9, part A as the starting acid to obtain the title product ($R_1$=benzyl, $Y_1$=NH—C(O)O—, A=benzene, $R_2$=fluorophenyl, $Y_2$=$CH_2$, m=0, p=1).

EXAMPLE 25

N-[5,8-Difluoro-1-Oxo-4-(2-Pyridyl)Phthalazin-2-yl]Benzamide

A. 3,6-Difluoro-2-(2-pyridylcarbonyl)benzoic acid 3,6-difluoro phthalic acid (50 mmol) is added to a Grignard solution of 2-bromomagnesium pyridine (25 mmol) in ether. The reaction mixture is stirred under reflux for 2 hours, is cooled with ice, and is then hydrolysed with HCl to yield 3,6-difluoro-2-(2-pyridylcarbonyl)benzoic acid.

B. 5,8-Difluoro-4-(2-pyridyl)-benzo[d]1,2-oxazin-1-one

The procedure described in Example 14, part A is followed with the above obtained benzoic acid as a starting material to produce the title compound.

C. 2-Amino-5,8-difluoro-4-(2-pyridyl)-(2H)-1-phthalazinone

The procedure described in Example 14, part B is followed with 5,8-difluoro-4-(2-pyridyl)-benzo[d]1,2-oxozin-1-one as the starting material to yield 2-amino-5,8-diflouro-4-(2-pyridyl)-(2H)-1-phthalazinone.

D. N-[5,8-Difluoro-1-oxo-4-(2-pyridyl)phthalazin-2-yl]benzamide

The product of part C, 2-amino-5,8-difluoro-4-(2-pyridyl)-(2H)-1-phthalazinone (0.01 mol) is stirred overnight with benzoylchloride in dichloromethane at room temperature. The product is recrystallized to yield the title compound ($R_1$=benzyl, $Y_1$=—NH—C(O), $R_2$=2-pyridyl, A=benzene, $R_3$=F, F, m=2, p=0).

Biological Effects (A) Growth Inhibition

The compounds of Examples 1–3 were assayed for their growth inhibitory activity on the human colon carcinoma cell line, SW-480 obtained from ATCC (Rockville, Md.), to ascertain the degree of growth inhibition. Growth inhibition of this cell line is indicative of a benefit on precancerous lesions and neoplasms. The cell line and growth assay employed for such experiments are well characterized, and are used to evaluate the anti-neoplastic properties of NSAIDs. The assay is used by the United States National Cancer Institute in its screening program for new anti-cancer drugs.

Drug stock solutions were made in 100% DMSO and were then diluted with RPMI media for cell culture testing. All drug solutions were prepared fresh on the day of testing. The cultured cells were obtained at passage #99 and grown in RPMI media supplemented with 5% fetal calf serum, and 2 mM glutamine, 100 u/ml penicillin, 100 U/ml streptomycin, and 0.25 µg/ml amphotericin. The cultures were maintained in a humidified atmosphere of 95% air and 5% $CO_2$ at 37° C. The cultures were passaged at preconfluent densities using a solution of 0.05% trypsin and 0.53 mM EDTA. Cells were plated at 1000 cells/well for 96 well flat-bottom microtiter plates.

Tumor cell growth inhibition was assessed using the Sulforhodamine B (SRB) protein binding assay. In this assay, tumor cells were plated in 96-well plates and treated with drug-containing media for six days (continuous exposure). For each plate, 6 wells were designated as no treatment controls, six wells as vehicle (0.1% DMSO) controls, and the remaining wells for drug dilutions with three wells per drug concentration. At the end of the exposure period, the cells were fixed and stained with sulforhodamine B, a protein binding dye. The dye was then solubilized, and the optical density of the resulting solution was determined on a 96-well plate reader. The mean dye intensity of the treated wells was then divided by the mean dye intensity in the control wells (6 wells of each) to determine the effect of the drug on the cells. Dye intensity is proportional to the number of cells or amount of protein per well. The resultant "percent inhibition" value then represents the degree of growth inhibition caused by the drug.

Percent inhibition values obtained for the compounds of Examples 1–3 are shown in Table 1.

TABLE 1

Growth inhibitory effects of compounds.

| EXAMPLE | % Growth Inhibition (100 μM) |
|---|---|
| 1 | 90.0% |
| 2 | −7.8% |
| 3 | 86.1% |

An $IC_{50}$ value was also determined for the compound of Example 3. This value is equivalent to the concentration of drug needed to inhibit tumor cell growth by 50% relative to a vehicle control. $IC_{50}$ value was obtained graphically by connecting the mean values for each drug concentration tested. Each experiment included at least three wells per drug concentration. Concentration was plotted on a log scale on the X-axis. The $IC_{50}$ value obtained for the compound of Example 3 is 5.18 μM. The values used to determine the $IC_{50}$ are shown in Table 2.

TABLE 2

| Dose (μM) | Growth Inhibition (% Vehicle ± SD) |
|---|---|
| 0 (vehicle) | 100 ± 10.4 |
| 0.001 | 105 ± 20 |
| 0.01 | 99 ± 11.9 |
| 0.1 | 91 ± 5.0 |
| 1.0 | 94 ± 17.9 |
| 10.0 | 34 ± 17.8 |
| 100.0 | 6 ± 1.6 |

(B) Apoptosis

Apoptosis was measured using an assay of cell death based on a characteristic feature of apoptotic cells (i.e., fragmented DNA). Briefly, SW-480 colon adenocarcinoma cells were plated in 96-well microtitre plates ("MTP") at a density of 10K cells/well in 180 μl and were incubated for 24 hrs. Cells were then treated with 20 μl aliquots of appropriately diluted compound, and allowed to incubate for an additional 48 hrs.

After the incubation, samples were prepared according to the following steps. The MTP was centrifuged (15 min., 1000 rpm) and the supernatant was carefully removed by fast inversion of the MTP. The cell pellets in each well were resuspended in 200 μl lysis buffer and incubated for 45 min. at room temperature to lyse the cells. The lysates were then centrifuged (15 min., 1000 rpm) and 20 μl aliquots of the supernatant (=cytoplasmic fraction) were transferred into the streptavidin coated MTP for analysis. Care was taken not to shake the lysed pellets in the MTP (=cell nucleii containing high molecular weight, unfragmented DNA). Samples were analyzed immediately, because storage at 4° C. or −20° C. reduces the ELISA-signals.

Samples were then processed according to a DNA fragmentation assay protocol, and dose-response curves were generated based on optical density readings. Quantification of DNA was done by a commercially available photometric enzyme-immunoassay manufactured by Mannheim-Boehringer under the name "Cell Death Detection ELISA$^{P-}$$_{lus}$". The assay is based on a quantitative sandwich-enzyme-immunoassay-principle using mouse monoclonal antibodies directed against DNA and histones, respectively. This allows the specific determination of mono and oligonucleosomes in the cytoplasmatic fraction of cell lysates. In brief, the assay procedure is as follows. The sample (cell-lysate, serum, culture-supernatant etc.) is placed into a streptavidin-coated MTP. Subsequently, a mixture of anti-histone-biotin and anti-DNA-POD is followed by incubation for 2 hours. During the incubation period, the anti-histone antibody binds to the histone-component of the nucleosomes and simultaneously fixes the immunocomplex to the streptavidin-coated MTP via its biotinylation. Additionally, the anti-DNA-POD antibody reacts with the DNA component of the nucleosomes. After removal of unbound antibodies by a washing step, the amount of nucleosomes is quantified by the POD retained in the immunocomplex. POD is determined photometrically with ABTS® (2,2'-Azino-di[3-ethylbenzthiazolin-sulfonat]) as substrate.

Fold stimulation (FS=ODmax/ODveh), an indicator of apoptotic response, was determined for each compound tested. The FS values for the tested compounds are listed in Table 3.

TABLE 3

| EXAMPLE | DNA Fragmentation FS (100 μM) |
|---|---|
| 1 | 7.3 |
| 2 | 1.2 |
| 3 | 6.1 |

In addition, using the DNA fragmentation test above, an $EC_{50}$ value for the compound of Example 3 was determined to be 7.2 μM. The $EC_{50}$ value obtained for the compound of Example 3 is 7.19 μM. The values used to determine the $EC_{50}$ are shown in Table 4.

TABLE 4

| Dose (μM) | Apoptosis Level (Mean OD Value ± SD) |
|---|---|
| 0 (vehicle) | 0.175 ± 0.02 |
| 0.001 | 0.156 ± 0.02 |
| 0.01 | 0.165 ± 0.03 |
| 0.1 | 0.161 ± 0.02 |
| 1.0 | 0.208 ± 0.01 |
| 10.0 | 1.789 ± 0.32 |
| 100.0 | 2.763 ± 0.29 |

The compounds of this invention can be formulated with pharmaceutically acceptable carriers into unit dosage forms in a conventional manner so that the patient in need of therapy for precancerous lesions can periodically (e.g., once or more per day) take a compound according to the methods of this invention. The exact initial dose of the compounds of this invention can be determined with reasonable experimentation. One skilled in the art should understand that the initial dosage should be sufficient to achieve a blood plasma concentration approaching a percentage of the $IC_{50}$ value of the compound, with the percentage depending on the chemopreventative or chemotherapeutic indication. The initial dosage calculation would also take into consideration several factors, such as the formulation and mode of administration, e.g. oral or intravenous, of the particular compound. For example, assuming a patient with an average circulatory system volume of about four liters, based on the IC$_{50}$ values for compounds of this invention, one would calculate a dosage of about 8.4 mg. of such compounds for intravenous administration to achieve a systemic circulatory concentration equivalent to the IC$_{50}$ concentration.

We claim:

1. A compound of the formula:

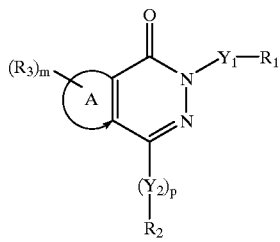

wherein Y$_1$ is selected from the group consisting of —(CH$_2$)$_n$—C(O)—NH—, —NH—, —NH—C(X)—O—, and —NH—C(O)—NH—; where X is oxygen or sulfur, and n is an integer from 1 to 3;

R$_1$ and R$_2$ are independently selected from the group consisting of substituted or unsubstituted phenyl, benzyl, pyridinyl, pyrrolidinyl, pyrazolyl, pyrazolidinyl, imidazolyl, imidazolidinyl, piperidinyl, pyrazinyl, piperazinyl, pyrimidinyl, morpholinyl, tetrazolyl, triazinyl, furfuryl and thiophenyl, wherein said substituents are one to three independently selected from the group consisting of halogen, lower alkyl, lower alkoxy, amino, lower alkylamino, di-lower alkylamino, hydroxy, nitro, nitrile, —CO$_2$H, —SO$_2$NH$_2$, lower alkyl mercapto, and lower alkyl sulfonyl;

Y$_2$ is selected from the group consisting of lower alkylene, lower (hydroxy) alkylene, lower (amino) alkylene, lower (alkylamino) alkylene, carbonyl, and —CH$_2$—NH—;

A is a ring fused with the pyridazine ring selected from the group consisting of benzene and pyridinyl;

R$_3$ is independently selected in each instance from the group consisting of halogen, lower alkyl, lower alkoxy, amino, lower alkylamino, di-lower alkylamino, hydroxy, nitro, nitrile, —CO$_2$H, —SO$_2$NH$_2$, lower alkyl mercapto, and lower alkyl sulfonyl;

m is an integer from 0 to four;

p is 0 or 1;

or pharmaceutically acceptable salts thereof.

2. The compound of claim 1 wherein R$_1$ is selected from the group consisting of substituted or unsubstituted phenyl, benzyl, pyridinyl, pyrrolyl, pyrazinyl, pyrimidinyl, morpholinyl, tetrazolyl, triazinyl, furfuryl and thiophenyl, wherein said substituents are one or two independently selected from the group consisting of halogen, lower alkyl, lower alkoxy, di-lower alkylamino, hydroxy, nitrile, —CO$_2$H, —SO$_2$NH$_2$, lower alkyl mercapto, and lower alkyl sulfonyl.

3. The compound of claim 1 wherein R$_2$ is selected from the group consisting of substituted or unsubstituted phenyl, benzyl, pyridinyl, pyrrolyl, pyrazolyl, imidazolyl, pyrazinyl, pyrimidinyl, morpholinyl, triazinyl, furfuryl and thiophenyl, wherein said substituents are one, two, or three independently selected from the group consisting of halogen, lower alkyl, lower alkoxy, di-lower alkylamino, hydroxy, nitro, lower alkyl mercapto, and lower alkyl sulfonyl.

4. The compound of claim 1 wherein Y$_2$ is selected from the group consisting of lower alkylene, lower (hydroxy) alkylene, carbonyl, and —CH$_2$—NH—.

5. The compound of claim 1 wherein p is 0 or 1.

6. The compound of claim 1 wherein p is 0.

7. The compound of claim 1 wherein R$_3$ is independently selected in each instance from the group consisting of halogen, lower alkyl, lower alkoxy, di-lower alkylamino, hydroxy, —CO$_2$H, —SO$_2$NH$_2$, lower alkyl mercapto, and lower alkyl sulfonyl; and m is an integer from 0 to 2.

8. The compound of claim 6 wherein R$_3$ is selected from the group consisting of halogen, lower alkyl, lower alkoxy, di-lower alkylamino, and lower alkyl mercapto; and m is 0 or 1.

9. A pharmaceutical composition comprising a pharmaceutically acceptable carrier and compound of the formula:

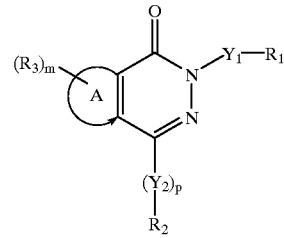

wherein Y$_1$ is selected from the group consisting of —(CH$_2$)$_n$—C(O)—NH—, —NH—, —NH—C(X)—O—, and —NH—C(O)—NH—; where X is oxygen or sulfur, and n is an integer from 1 to 3;

R$_1$ and R$_2$ are independently selected from the group consisting of substituted or unsubstituted phenyl, benzyl, pyridinyl, pyrrolidinyl, pyrazolyl, pyrazolidinyl, imidazolyl, imidazolidinyl, piperidinyl, pyrazinyl, piperazinyl, pyrimidinyl, morpholinyl, tetrazolyl, triazinyl, furfuryl and thiophenyl, wherein said substituents are one to three independently selected from the group consisting of halogen, lower alkyl, lower alkoxy, amino, lower alkylamino, di-lower alkylamino, hydroxy, nitro, nitrile, —CO$_2$H, —SO$_2$NH$_2$, lower alkyl mercapto, and lower alkyl sulfonyl;

Y$_2$ is selected from the group consisting of lower alkylene, lower (hydroxy) alkylene, lower (amino) alkylene, lower (alkylamino) alkylene, carbonyl, and —CH$_2$—NH—;

A is a ring fused with the pyridazine ring selected from the group consisting of benzene and pyridinyl;

R$_3$ is independently selected in each instance from the group consisting of halogen, lower alkyl, lower alkoxy, amino, lower alkylamino, di-lower alkylamino, hydroxy, nitro, nitrile, —CO$_2$H, —SO$_2$NH$_2$, lower alkyl mercapto, and lower alkyl sulfonyl;

m is an integer from 0 to four;

p is 0 or 1;

or pharmaceutically acceptable salts thereof.

10. The pharmaceutical composition of claim 9 wherein R$_1$ is selected from the group consisting of substituted or unsubstituted phenyl, benzyl, pyridinyl, pyrrolyl, pyrazinyl, pyrimidinyl, morpholinyl, tetrazolyl, triazinyl, furfuryl and thiophenyl, wherein said substituents are one or two independently selected from the group consisting of halogen, lower alkyl, lower alkoxy, di-lower alkylamino, hydroxy, nitrile, —CO$_2$H, —SO$_2$NH$_2$, lower alkyl mercapto, and lower alkyl sulfonyl.

11. The pharmaceutical composition of claim 9 wherein R$_2$ is selected from the group consisting of substituted or unsubstituted phenyl, benzyl, pyridinyl, pyrazolyl, imidazolyl, pyrazinyl, pyrimidinyl, morpholinyl, triazinyl, furfuryl and thiophenyl, wherein said substituents are one, two, or three independently selected from the group consisting of halogen, lower alkyl, lower alkoxy, di-lower alkylamino, hydroxy, nitro, lower alkyl mercapto, and lower alkyl sulfonyl.

12. The pharmaceutical composition of claim 9 wherein Y$_2$ is selected from the group consisting of lower alkylene, lower (hydroxy) alkylene, carbonyl, and —CH$_2$—NH—.

13. The pharmaceutical composition of claim 9 wherein p is 0 or 1.

14. The pharmaceutical composition of claim 9 wherein R$_3$ is independently selected in each instance from the group consisting of halogen, lower alkyl, lower alkoxy, di-lower alkylamino, hydroxy, —CO$_2$H, —SO$_2$NH$_2$, lower alkyl mercapto, and lower alkyl sulfonyl; and m is an integer from 0 to 2.

15. A method of treating a patient having neoplasia comprising administering to a patient with neoplasia sensitive to such a compound a pharmacologically effective amount of a compound of the formula:

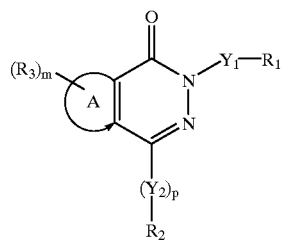

wherein Y$_1$ is selected from the group consisting of —(CH$_2$)$_n$—C(X)—NH—, —NH—, —NH—C(X)—, —NH—C(X)—O—, and —NH—C(X)—NH—; where X is oxygen or sulfur, and n is an integer from 0 to 3;

R$_1$ and R$_2$ are independently selected from the group consisting of substituted or unsubstituted phenyl, benzyl, pyridinyl, pyrrolyl, pyrrolidinyl, pyrazolyl, pyrazolidinyl, imidazolyl, imidazolidinyl, piperidinyl, pyrazinyl, piperazinyl, pyrimidinyl, morpholinyl, tetrazolyl, triazinyl, furfuryl and thiophenyl, wherein said substituents are one to three independently selected from the group consisting of halogen, lower alkyl, lower alkoxy, amino, lower alkylamino, di-lower alkylamino, hydroxy, nitro, nitrile, —CO$_2$H, —SO$_2$NH$_2$, lower alkyl mercapto, and lower alkyl sulfonyl;

Y$_2$ is selected from the group consisting of lower alkylene, lower (hydroxy) alkylene, lower (amino) alkylene, lower (alkylamino) alkylene, carbonyl, and —CH$_2$—NH—;

A is a ring fused with the pyridazine ring selected from the group consisting of benzene and pyridinyl;

R$_3$ is independently selected in each instance from the group consisting of halogen, lower alkyl, lower alkoxy, amino, lower alkylamino, di-lower alkylamino, hydroxy, nitro, nitrile, —CO$_2$H, —SO$_2$NH$_2$, lower alkyl mercapto, and lower alkyl sulfonyl.

m is an integer from 0 to four;

p is 0 or 1;

or pharmaceutically acceptable salts thereof.

16. The method of claim 15 wherein R$_1$ is selected from the group consisting of substituted or unsubstituted phenyl, benzyl, pyridinyl, pyrrolyl, pyrazinyl, pyrimidinyl, morpholinyl, tetrazolyl, triazinyl, furfuryl and thiophenyl, wherein said substituents are one or two independently selected from the group consisting of halogen, lower alkyl, lower alkoxy, di-lower alkylamino, hydroxy, nitrile, —CO$_2$H, —SO$_2$NH$_2$, lower alkyl mercapto, and lower alkyl sulfonyl.

17. The method of claim 15 wherein R$_2$ is selected from the group consisting of substituted or unsubstituted phenyl, benzyl, pyridinyl, pyrrolyl, pyrazolyl, imidazolyl, pyrazinyl, pyrimidinyl, morpholinyl, triazinyl, furfuryl and thiophenyl, wherein said substituents are one, two, or three independently selected from the group consisting of halogen, lower alkyl, lower alkoxy, di-lower alkylamino, hydroxy, nitro, lower alkyl mercapto, and lower alkyl sulfonyl.

18. The method of claim 15 wherein Y$_2$ is selected from the group consisting of lower alkylene, lower (hydroxy) alkylene, carbonyl, and —CH$_2$—NH—.

19. The method of claim 15 wherein p is 0 or 1.

20. The method of claim 15 wherein R$_3$ is independently selected in each instance from the group consisting of halogen, lower alkyl, lower alkoxy, di-lower alkylamino, hydroxy, —CO$_2$H, —SO$_2$NH$_2$, lower alkyl mercapto, and lower alkyl sulfonyl; and m is an integer from 0 to 2.

21. The method of claim 15 wherein R$_3$ is selected from the group consisting of halogen, lower alkyl, lower alkoxy, di-lower alkylamino, and lower alkyl mercapto; and m is 0 or 1.

22. A method for inhibiting the growth of neoplastic cells comprising exposing neoplastic cells sensitive to such a compound to a growth inhibiting effective amount of a compound of the formula:

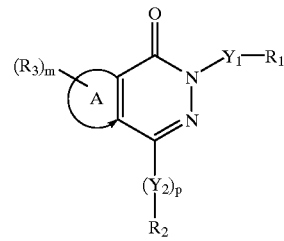

wherein Y$_1$ is selected from the group consisting of —(CH$_2$)$_n$—C(X)—NH—, —NH—, —NH—C(X)—, —NH—C(X)—O—, and —NH—C(X)—NH—; where X is oxygen or sulfur, and n is an integer from 0 to 3;

R$_1$ and R$_2$ are independently selected from the group consisting of substituted or unsubstituted phenyl, benzyl, pyridinyl, pyrrolyl, pyrrolidinyl, pyrazolyl, pyrazolidinyl, imidazolyl, imidazolidinyl, piperidinyl, pyrazinyl, piperazinyl, pyrimidinyl, morpholinyl, tetrazolyl, triazinyl, furfuryl and thiophenyl, wherein said substituents are one to three independently selected from the group consisting of halogen, lower alkyl, lower alkoxy, amino, lower alkylamino, di-lower alkylamino, hydroxy, nitro, nitrile, —CO$_2$H, —SO$_2$NH$_2$, lower alkyl mercapto, and lower alkyl sulfonyl;

Y$_2$ is selected from the group consisting of lower alkylene, lower (hydroxy) alkylene, lower (amino)

alkylene, lower (alkylamino) alkylene, carbonyl, and —CH$_2$—NH—;

A is a ring fused with the pyridazine ring selected from the group consisting of benzene and pyridinyl;

R$_3$ is independently selected in each instance from the group consisting of halogen, lower alkyl, lower alkoxy, amino, lower alkylamino, di-lower alkylamino, hydroxy, nitro, nitrile, —CO$_2$H, —SO$_2$NH$_2$, lower alkyl mercapto, and lower alkyl sulfonyl;

m is an integer from 0 to four;

p is 0 or 1;

or pharmaceutically acceptable salts thereof.

23. The method of claim 22 wherein R$_2$ is selected from the group consisting of substituted or unsubstituted phenyl, benzyl, pyridinyl, pyrrolyl, pyrazolyl, imidazolyl, pyrazinyl, pyrimidinyl, morpholinyl, triazinyl, furfuryl and thiophenyl, wherein said substituents are one, two, or three independently selected from the group consisting of halogen, lower alkyl, lower alkoxy, di-lower alkylamino, hydroxy, nitro, lower alkyl mercapto, and lower alkyl sulfonyl.

24. A method for inducing apoptosis in neoplasic cells comprising exposing cells sensitive to such a compound to an effective amount of a compound of the formula:

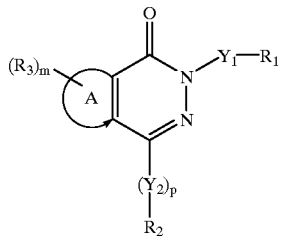

wherein Y$_1$ is selected from the group consisting of —(CH$_2$)$_n$—C(X)—NH—, —NH—, —NH—C(X)—, —NH—C(X)—O—, and —NH—C(X)—NH—; where X is oxygen or sulfur, and n is an integer from 0 to 3;

R$_1$ and R$_2$ are independently selected from the group consisting of substituted or unsubstituted phenyl, benzyl, pyridinyl, pyrrolyl, pyrrolidinyl, pyrazolyl, pyrazolidinyl, imidazolyl, imidazolidinyl, piperidinyl, pyrazinyl, piperazinyl, pyrimidinyl, morpholinyl, tetrazolyl, triazinyl, furfuryl and thiophenyl, wherein said substituents are one to three independently selected from the group consisting of halogen, lower alkyl, lower alkoxy, amino, lower alkylamino, di-lower alkylamino, hydroxy, nitro, nitrile, —CO$_2$H, —SO$_2$NH$_2$, lower alkyl mercapto, and lower alkyl sulfonyl;

Y$_2$ is selected from the group consisting of lower alkylene, lower (hydroxy) alkylene, lower (amino) alkylene, lower (alkylamino) alkylene, carbonyl, and —CH$_2$—NH—;

A is a ring fused with the pyridazine ring selected from the group consisting of benzene and pyridinyl;

R$_3$ is independently selected in each instance from the group consisting of halogen, lower alkyl, lower alkoxy, amino, lower alkylamino, di-lower alkylamino, hydroxy, nitro, nitrile, —CO$_2$H, —SO$_2$NH$_2$, lower alkyl mercapto, and lower alkyl sulfonyl;

m is an integer from 0 to four;

p is 0 or 1;

or pharmaceutically acceptable salts thereof.

* * * * *